United States Patent [19]
Davis

[11] Patent Number: 4,667,675
[45] Date of Patent: May 26, 1987

[54] RETENTION SUTURE APPARATUS

[76] Inventor: Emsley A. Davis, 1616 Colcord Ave., Waco, Tex. 76707

[21] Appl. No.: 836,992

[22] Filed: Mar. 6, 1986

[51] Int. Cl.$^4$ ............................................. A61B 17/08
[52] U.S. Cl. ............................... 128/335; 128/334 C; 128/337; 24/71.1
[58] Field of Search ............... 128/335, 334 C, 334 R, 128/337; 24/71.1, 71.2

[56] References Cited

U.S. PATENT DOCUMENTS

| | | | |
|---|---|---|---|
| 3,650,274 | 3/1972 | Edwards et al. | 128/335 |
| 3,831,608 | 8/1974 | Kletschka et al. | 128/335 |
| 3,931,821 | 1/1976 | Kletschka et al. | 128/335 |
| 4,535,772 | 8/1985 | Sheehan | 128/335 |

*Primary Examiner*—Richard C. Pinkham
*Assistant Examiner*—Gary Jackson
*Attorney, Agent, or Firm*—Arthur F. Zobal

[57] ABSTRACT

The retention suture apparatus is employed for maintaining a wound closed with a retention suture. The apparatus includes a relatively flat and stiff bridging member adapted to be placed across the wound. One end of the bridging member is adapted to have one end of the suture coupled thereto with the suture extending through the skin on one side of the wound, passing transversely to the wound under the skin and tissue and exiting from the skin on the other side of the wound such that its free end may engage the other end of the bridging member. A plurality of apertures are formed through the bridging member on each side of a central portion. The apparatus also includes a bowed resilient fastening member having hooks at its two ends and a wrapping projection extending transversely from its convex side. The free end of the suture is wrapped around the projection and then tied to the fastening member. The fastening member is removably coupled to the bridging member by straightening the fastening member to increase the distance between its hooks to allow its hooks to be inserted into a selected set of the apertures of the bridging member depending upon the tension on the suture desired. The fastening member then is allowed to resume its normal bowed shape to allow its hooks to securely engage the edges of the selected apertures.

11 Claims, 9 Drawing Figures

RETENTION SUTURE APPARATUS

FIELD OF INVENTION

The present invention relates to surgical devices, particularly those devices that are used in conjunction with retention sutures.

DESCRIPTION OF THE PRIOR ART

In abdominal surgery, complications concerning wound dehiscence can arise after the surgical incision has been stitched closed. When a wound dehisces, or bursts open, a potentially fatal situation results, particularly in high risk patients. Retention sutures placed transversely across the wound are used to prevent the occurrence of wound dehiscence by promoting wound closure. A single retention suture generally penetrates the skin and the several adjacent tissue layers at a point several centimeters to one side of the wound. The retention suture then traverses through the abdominal tissues, crosses the wound, and finally emerges on the opposite side of and several centimeters away from the wound.

While retention sutures solve some problems of abdominal surgery, several new problems are created. As the wound area swells, the tension of the suture increases, often resulting in damage to the underlying skin. Buttons and soft rubber tubes are prior art devices that are used to raise the sutures off of the skin and distribute the tension over a larger skin area. Buttons, however, do not prevent skin damage, while rubber tubes increase the difficulty of suture removal, among other problems.

Another prior art device, exemplified by U.S. Pat. No. 3,650,274, is the retention suture bridge. A retention suture bridge spans the wound and distributes the pressure caused by the suture over a larger area of skin than do buttons and tubes, thereby greatly alleviating the problems caused by high suture tension. In addition to distributing the pressure of suture tension over a relatively larger area, several other aspects are desirable in a bridging device. Adjustments of suture tension are frequently necessary, therefore a retention suture bridge device should provide for tension adjustment with a minimum of difficulty. Further, since retention suture bridges cover the wound, periodic removal is required to allow access to the wound area for inspection and treatment. Thus a retention suture bridge device should lend itself to removal and replacement.

SUMMARY OF THE INVENTION

It is an object of the present invention to provide a retention suture apparatus that can be easily disassembled and removed from the wound area.

It is another object of the present invention to provide a retention suture apparatus that will allow the adjustment of suture tension with a minimum of difficulty.

The retention suture apparatus of the invention comprises a bridging member having two ends with a central portion intermediate its two ends and two opposite facing sides. The bridging member is adapted to be placed across the wound such that one of its sides faces the skin of the patient and its ends are on opposite sides of the wound with the central portion above the wound. One of the ends of the bridging member is adapted to have one end of a retention suture coupled thereto with the suture may extending through the skin on one side of the wound, passing through the wound under the skin and tissue, exiting from the skin on the other side of the wound such that it may engage the other end of the bridging member. A fastening member is provided which has two ends and first and second opposite facing sides. Projection means extend transversly from the first side of the fastening member intermediate its ends. The fastening member and the bridging member include means to allow the fastening member to be removably coupled to the bridging member such that the first side and the projection means of the fastening member face away from the bridging member whereby the suture may be extended from said other end of said bridging member to said projection means, wrapped around said projection means and the other end of the suture coupled to said fastening means.

In a another aspect, the means which allow the fastening member to be removably coupled to the bridging member comprises at least one set of two apertures extending through the bridging member between its two opposite sides such that one of the apertures is formed between the central portion and one end of the bridging member and the other aperture is formed between the central portion and the other end of the bridging member. Hooks are formed at the ends of the fastening member such that they may be removably located in the apertures of the bridging member to removably couple the fastening member to the bridging member.

In a further aspect, the fastening member is normally bowed in shape and the hooks extend from the concave side of the fastening member at its two ends in a direction generally transverse to its length and then toward each other terminating in hook ends which generally face each other. The minimum distance between the two apertures of the bridging member is greater than the distance between the two hook ends of the fastening member when the fastening member is in its normal bowed shape. The fastening member may be coupled to the bridging member by applying force to the fastening member to straighten the fastening member to increase the distance between the hook ends of the hooks to allow the hooks to be inserted into the apertures of the bridging member. When the force is released, the fastening member resumes its normally bowed shape to allow the hooks to engage the structure of the bridging member which define the edges of the two apertures closest to each other. In the preferred embodiment, a plurality of sets of apertures are formed through the bridging member whereby the hooks may be inserted into a selected one of the sets of apertures depending upon the tension of the suture desired.

DESCRIPTION OF THE PREFERRED EMBODIMENT

Figure 1:
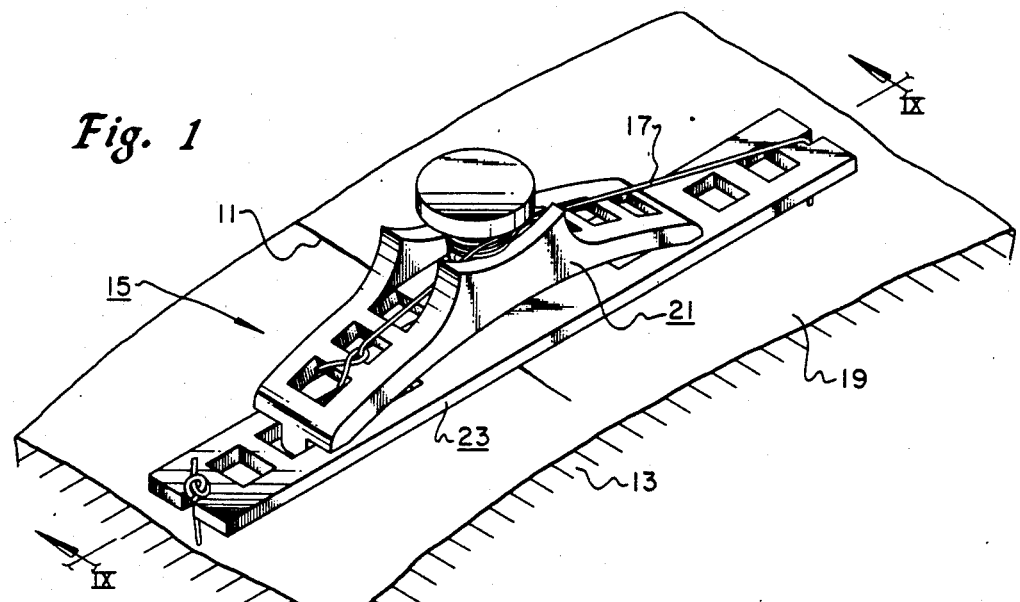
FIG. 1 is a schematic isometric view showing a surgical retention suture apparatus of the present invention in place over a wound.
Figure 2:
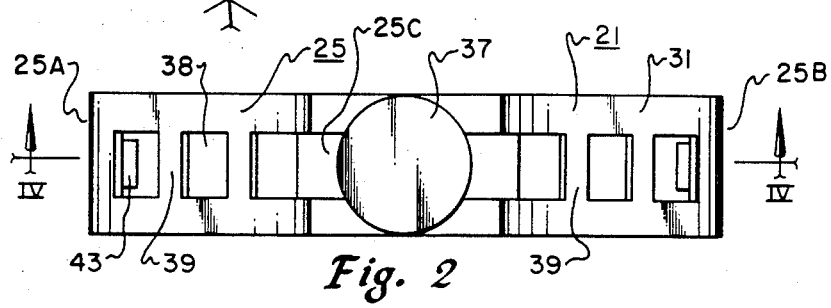
FIG. 2 is a top plan view of the fastening member of the apparatus.
Figure 3:
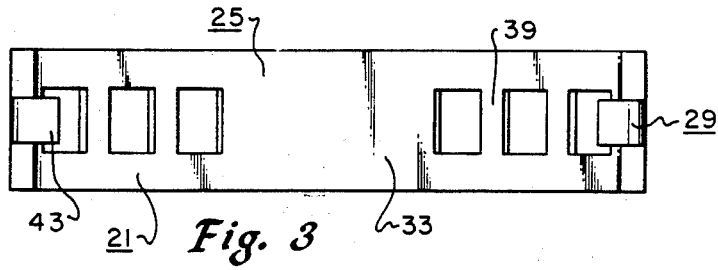
FIG. 3 is a bottom plan view of the fastening member.
Figure 4:
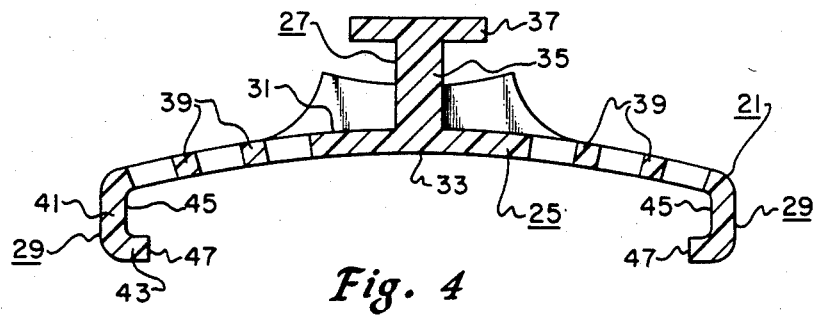
FIG. 4 is a longitudinal cross-sectional view taken at lines IV—IV of FIG. 2.

In FIG. 1 there is shown an isometric view of a portion of a wound formed by a surgical incision through abdominal tissues 13. Also shown is the surgical retention suture apparatus or device 15 of the invention and a retention suture 17 for closing the wound. The suture 17 is a flexible strand which may be formed of nylon. As shown in FIGS. 6-9, the suture 17 passes through the skin a short distance on each side of the wound 11 and beneath the skin through the tissue transverse to the wound in accordance with acceptable surgical practices. In a typical wound closure, several retention sutures 17, each held in place by one of the devices 15, will be utilized along the length of the wound.

The surgical retention suture apparatus 15 of the invention will now be described with particular reference to FIGS. 2-5. The surgical retention suture apparatus 15 includes a fastening member 21, a bridging member 23, and means for removably coupling the fastening member to the bridging member.

The fastening member 21 comprises a strip portion 25 which has two ends 25A and 25B and is normally arcuate or bowed from end to end forming a convex top surface 31 and a concave bottom surface 33. A wrapping projection 27 comprising a post or stem 35 and an enlarged head or cap 37 extends transversely from a central portion 25C of side 31 intermediate the ends 25A and 25B. The post 35 is cylindrical in shape and the cap 37 is a round disc-like member. Three spaced apart apertures 38 are formed through the strip portion 25 on each side of the central portion 25C. Transverse struts 39 extend between adjacent apertures 38 on each side of the central portion 25C.

Hooks 29 each of which comprises a shank 41 and a curved portion 43, extend from the side 33 of the fastening member 21 at the ends 25A and 25B. The shanks 41 extend in a direction generally transverse to the length of the member 21 and the curved portions 43 curve toward each other terminating in surfaces 47 which face each other.

The fastening member is made of relatively flexible and resilient material such that the strip portion 25 may be straightened, to increase the distance between the surfaces 47 of the hooks 29, and then released wherein the strip portion 25 resumes its normal bowed or arcuate shape.

The bridging member 23 is an elongated strip having two ends 23A and 23B, a central portion 23C intermediate its ends, and opposite facing planar surfaces 51 and 53. The thickness of member 23 between surfaces 51 and 53 is uniform and is less than the length of the inboard surfaces 45 of the shanks 41 of the hooks 29 of member 21. Slots or notches 55 are formed in the member 23 at its ends 23A and 23B for use for retaining one end of the retention suture 17 and for guiding the suture 17 as it leaves the skin and extends to the fastening member 21. The bridging member 23 is made of a relatively stiff material such that when suture tension is applied to the end portions of the member 23, little deformity is experienced in the thin plane of the member between surfaces 51 and 53.

Figure 5:
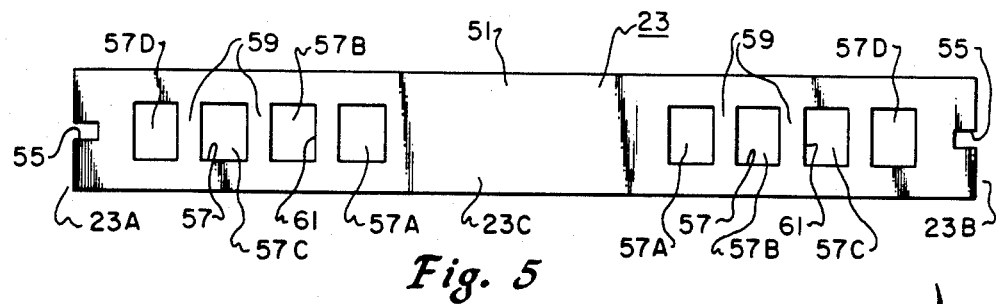
FIG. 5 is a plan view of the bridging member of the apparatus.
Figure 6:
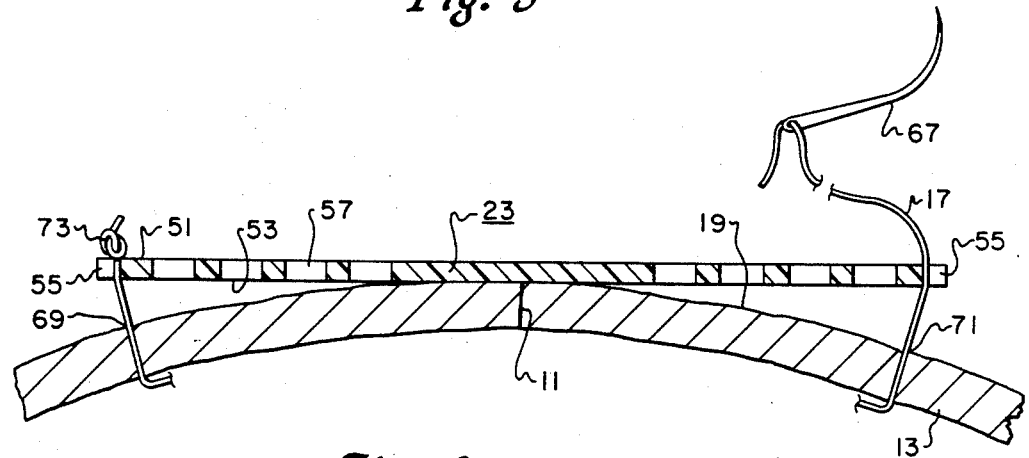
FIGS. 6–8 are schematic longitudinal cross-sectional views illustrating various steps in using the surgical retention suture apparatus of FIG. 1.
Figure 8:
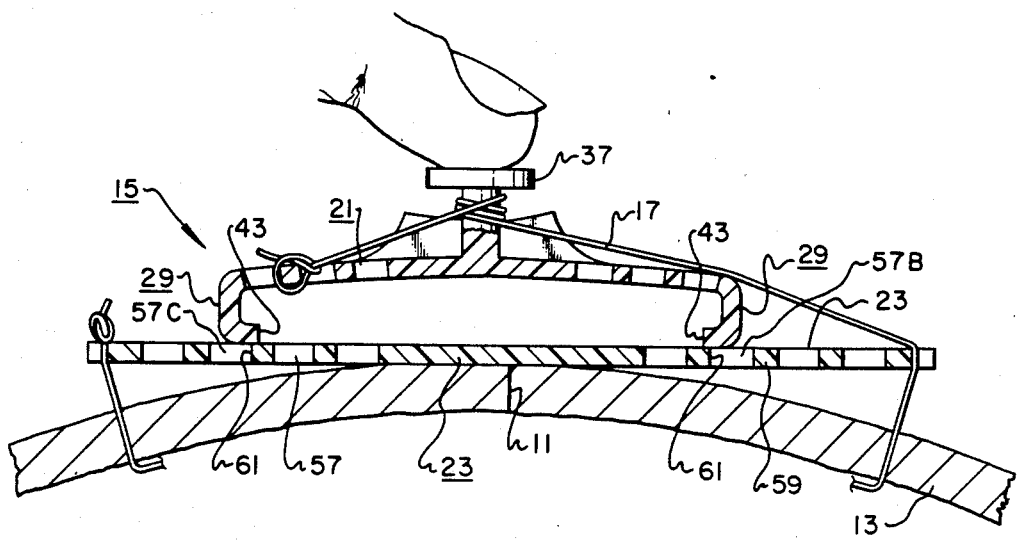
Figure 9:
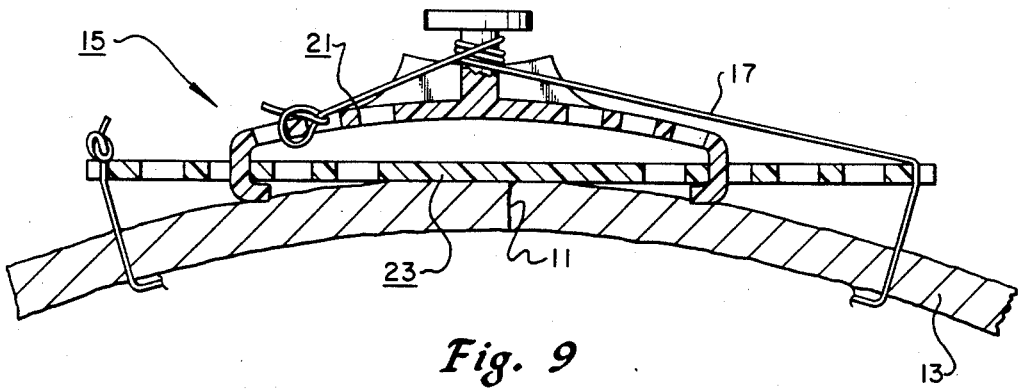
FIG. 9 is a schematic longitudinal cross-sectional view taken at lines IX—IX of FIG. 1.

The bridging member 23 has a plurality of longitudinally arranged rectangular shaped apertures 57 extending through the member 21 between surfaces 51 and 53 on each side of the center portion 23C of the member 23. Apertures 57 are spaced apart with transverse struts 59 extending between adjacent apertures 57 on each side of the central portion 23C. In FIG. 5, the apertures 57 on each side of the central portion 23C located progressively outward have been identified as 57A, 57B, 57C, and 57D. The apertures 57 each are of a size to allow the passage of the fastener hooks 29. The hooks 29 and bridging element struts 59 are sized to matingly engage each other. The apertures 57 and their struts 59 are arranged into sets for receiving the hooks 29, a set of apertures comprising one aperture on each side of the center portion 23C of the anchor piece 23. For example as shown in FIG. 8, one set of apertures 57 is formed by apertures 57B and 57C. The distance between the outboard edges 61 of the struts of a set of apertures 57 is slightly less than the distance between the inboard surfaces 45 of the shank portions 41 of the fastener hooks 29 but greater than the distances between surfaces 47 of the hooks 29, when the fastening member 21 is in its normally bowed position.

The use of the retention suture apparatus 15 will now be described, with reference to FIGS. 6-9. A needle 67, attached to an end portion of a length of suture material 17, is passed through the skin 19 and underlying abdominal tissues 13 on one side of the wound 11 at a point of entry 69 which is located several centimeters away from the wound 11. After configuring the suture 17 through the abdominal tissues 13 in accordance with acceptable surgical practices, the needle 67 exits the abdominal tissues 13 and skin 19 at a point of exit 71 on the opposite side of the wound 11. The point of exit 71 of the suture 17 is located at approximately the same distance away from the wound 11 as is the point of entry 69.

The bridging member 23 is next laid transversely across the wound 11 and over the dressing sheets (not shown) with its surface 53 facing the skin 19. The member 23 is aligned with the retention suture 17 such that its slots 55 overlie a line intersecting the point of entry 69 and the point of exit 71 with the slots being 55 equidistant from the point of entry and the point of exit. The end of the suture 17 nearest the point of entry 69 is knotted in a large ball 73 and the suture is placed inside of the nearest slot 55 such that the knot is on the top surface 51 of the member 23. To keep the knot 73 from slipping through the retaining slot 55, the knot should be larger than the width of the slot. The needle end portion of the suture is then brought through the guide slot 55 at the other end of the member 23. The needle 67 is removed from the suture leaving a lengthy piece of suture remaining.

Figure 7:
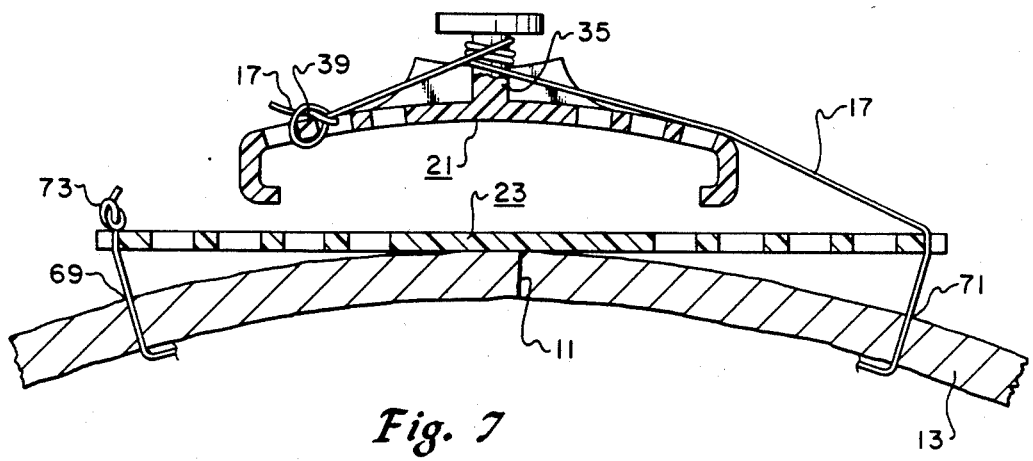

Next, the fastening member 21 is aligned with the bridging member 23 such that the surface 33 of member 21 faces the surface 51 of member 23 (see FIG. 7). The free end of the suture 17 is wrapped several times around the post 35 to achieve the desired suture tension. The free end of the suture is then tied to one of the struts 39 of the fastening member 21 on the side of the member 21 nearest the suture point of entry 69 into the skin.

With the hooks 29 of the fastening member 21 resting on the top surface 51 of the bridging member 23, downward force or pressure is applied to the cap 37 causing the fastening member 21 to straighten out (see FIG. 8). This in turn causes the distance between the inwardmost surfaces 47 of the hooks 29 to increase until it exceeds the distance between the outboard surfaces 61 of the struts 59 of the selected set of apertures 57. Usually one hook 29 will fall through an aperture 57 before the fastening member fully straightens out. This is followed by the other hook falling through the other aperture 57 of the set on the other side of the central portion 23C once the fastening member has been sufficiently straightened. When both hooks engage the outboard surfaces 61 of the struts 59 of the selected apertures 57, pressure is released from the cap, allowing the fastening member to regain its bowed shape. The fastening member 21 is now coupled or buckled in place to the bridging member 23 such that the position of the wrapping projection 27 relative to the guide slot 55 remains constant. The fastening member and the bridging member are locked together since the inboard surfaces 45 of the shank portions abut the outboard surfaces 61 of the struts 59 and the curved portions 43 are beneath the same struts (see FIG. 9). The fastening member may be removed or unbuckled from the bridging member by performing the above related steps in reverse order.

Several aspects of the present invention will now be discussed. During the healing process, suture tension will usually have to be adjusted periodically. One method of adjusting suture tension by utilizing the surgical retention suture apparatus 15 is to unwind the suture a sufficient number of times from around the post 35 until the desired tension is achieved. In this adjustment method, the suture 17 may be untied from and then retied to the strut 39. Another method of adjusting the suture tension is to uncouple the fastening member 21 from the bridging member 23 and move the hooks 29 of the fastening member 21 into a different set of apertures 57 before recoupling.

Frequent cleaning and inspection of the wound is required thus necessitating the easy removal of the surgical retention suture apparatus 15. Once unbuckled from the bridging member, the fastening member can be laid aside with the suture still attached. The bridging member can be completely removed from the wound area by removing the suture ends from the slots or notches 55. Recoupling the ends of the suture is easily done. The ends of the suture need not be retied to achieve the proper tension since in this case the ends were not untied. Normally several retention suture bridges are spaced several centimeters apart along the length of the wound. In accessing the wound, every other retention suture bridge should be left intact to maintain the integrity of wound closure.

Another important aspect of the invention is that by using a bridging member of sufficient length so that the distance between the slots or notches 55 is just slightly longer than the distance between the point of entry and the point of exit, the angle of the suture to the skin as the suture emerges from the abdominal tissues is close to a right angle to avoid the suture cutting into the skin. This angle can be maintained on small adults or children by either using a shorter bridging member and a correspondingly smaller fastening member, or by tying one end of the suture to a fastening member strut 59 and passing the other end portion of the suture through an aperture 57 at the other end portion of the bridging member. Either of the surfaces 51 or 53 of the bridging member 23 can be employed to face the skin and the fastening member 21 can be coupled to the bridging member 23 such that its ends 25A and 25B are close to ends 23A and 23B or 23B and 23A respectively of member 23. Since the surface 51 or 53 of the stiff bridging member 23 that faces the sking is planar, the abdomen is allowed to expand and contract without being hampered by a rigid curved bridge device while maintaining a 90 degree angle between the suture and the moving skin.

Another important aspect of the invention is the use of the device to bring the wound edges together if a deficit had occurred as a result of extensive debridgement secondary to extensive wound infection.

In one embodiment the fastening member 21 and bridging member 23 may be formed of suitable teflon or other suitable plastic material.

The foregoing disclosure and the showings made in the drawings are merely illustrative of the principles of this invention and are not to be intrepreted in a limiting sense.

I claim:

1. Apparatus for use with a retention suture for maintaining a wound of a patient closed, comprising:
    a bridging member having two ends with a central portion intermediate its two ends, and two opposite facing sides,
    said bridging member being adapted to be placed across the wound such that one of its sides faces the skin of the patient and its ends are on opposite sides of the wound with said central portion above the wound,
    one of said ends of said bridging member being adapted to have one end of a retention suture coupled thereto with the suture extending through the skin on one side of the wound, passing transversely to the wound under the skin and tissue, and exiting from the skin on the other side of the wound such that it may engage the other end of said bridging member,
    a fastening member having two ends and first and second opposite facing sides,
    projection means extending transversely from said first side of said fastening member intermediate its ends,
    said fastening member and said bridging member including means to allow said fastening member to be removably coupled to said bridging member such that said first side and said projection means of said fastening member face away from said bridging member whereby the suture may be extended from said other end of said bridging member to said projection means, wrapped around said projection means and the other end of the suture coupled to said fastening member.

2. The apparatus of claim 1, wherein said means of said fastening member and said bridging member which allow said fastening member to be removably coupled to said bridging member, comprises,
    at least one set of two apertures extending through said bridging member between its two opposite sides,
    one of said apertures being formed between said central portion and one end of said bridging member and the other of said apertures being formed between said central portion and the other end of said bridging member, and
    hooks formed at the ends of said fastening member such that they may be removably located in said apertures of said bridging member to removably couple said fastening member to said bridging member.

3. The apparatus of claim 2, wherein:
    said fastening member is normally bowed in shape between its two ends as seen in a plane extending through said first and second sides and said two ends of said fastening member such that said first and second sides normally are convex and concave, respectfully, as seen in said plane extending through said first and second sides and said two ends of said fastening member, said hooks extend from said second side of said fastening member at its two ends in a direction generally transverse to the dimension of said fastening member between its two ends and then toward each other terminating in hook ends which generally face each other, the minimum distance between said two apertures of said bridging member is greater than the distance between said two hook ends of said fastening member when said fastening member is in its normal bowed shape, the material of said fastening member being characterized such that force may be applied to said fastening member to straighten said fastening member and when the force is released, said fastening member resumes its normally bowed shape whereby said fastening member may be removably coupled to said bridging member by applying force to said fastening member to straighten said fastening member to increase the distance between said hook ends of said hooks to allow said hooks to be inserted into said apertures of said bridging member and then releasing the force to allow said hooks to engage the structure of said bridging member which define the edges of said two apertures closest to each other.

4. The apparatus of claim 3, comprising:
slots formed in said two ends of said bridging member for receiving the suture as it passes through the skin.

5. The apparatus of claim 3, wherein said projection means comprises a stem fixed to said fastening member and an enlarged head whereby force may be applied to the central portion of said fastening member by way of said enlarged head to straighten said fastening member to allow its hooks to be inserted into the apertures of said bridging member.

6. The apparatus of claim 3 comprising at least one suture receiving aperture extending through said fastening member between its first and second sides whereby the other end of the suture, after being wrapped around said projection means, may be inserted through said suture receiving aperture and tied to said fastening member.

7. The apparatus of claim 3 wherein said bridging member is made of a relatively stiff material and said one side of said bridging member is planar.

8. The apparatus of claim 3, comprising:
a plurality of sets of two apertures extending through said bridging member between its two opposite sides,
one of said apertures of each set being formed between said central portion and one end of said bridging member and the other of said apertures of each set being formed between said central portion and the other end of said bridging member whereby a plurality of spaced apart apertures extend in a line on each side of said central portion of said bridging member,
the minimum distance between the two apertures of each set being greater than the distance between said two hook ends of said hooks of said fastening member when said fastening member is in its normal bowed shape whereby said hooks of said fastening member may be inserted into a selected one of said plurality of sets of apertures, after the other end of the suture is wrapped around said projection means and coupled to said fastening member, depending on the tension desired on the suture.

9. The apparatus of claim 8, comprising:
slots formed in said two ends of said bridging member for receiving the suture as it passes through the skin,
said projection means comprising a stem fixed to said fastening member and an enlarged head whereby force may be applied to the central portion of said fastening member by way of said enlarged head to straighten said fastening member to allow its hooks to be inserted into the selected set of apertures of said bridging member, and
at least one suture receiving aperture extending through said fastening member between its first and second sides whereby the other end of the suture, after being wrapped around said projection means, may be inserted through said suture receiving aperture and tied to said fastening member,
said bridging member is made of a relatively stiff material and said one side of said bridging member is planar.

10. Apparatus for use with a retention suture for maintaining a wound of a patient closed, comprising:
a bridging member having two ends with a central portion intermediate its two ends, and two opposite facing sides,
said bridging member being adapted to placed across the wound such that one of its sides faces the skin of the patient and its ends are on opposite sides of the wound with said central portion above the wound,
one of said ends of said bridging member being adapted to have one end of a retention suture coupled thereto with the suture extending through the skin on one side of the wound, passing transversely to the wound under the skin and tissue, and exiting from the skin on the other side of the wound such that it may engage the other end of said bridging member,
at least one set of two apertures extending through said bridging member between its two opposite sides,
one of said apertures being formed between said central portion and one end of said bridging member and the other of said apertures being formed between said central portion and the other end of said bridging member, and
a fastening member having two ends and first and second opposite facing sides,
retaining means on said fastening member to which said other end of the suture can be tied,
hooks formed at the ends of said fastening member such that they may be removably located in said apertures of said bridging member to removably couple said fastening member to said bridging member such that said first side of said fastening member faces away from said bridging member whereby the suture may be extended from said other end of said bridging member to said retaining means and the other end of the suture coupled to said retaining means.

11. The apparatus of claim 10, comprising:

a plurality of sets of two apertures extending through said bridging member between its two opposite sides, one of said apertures of each set being formed between said central portion and one end of said bridging member and the other of said apertures of each set being formed between said central portion and the other end of said bridging member whereby a plurality of spaced apart apertures extend in a line on each side of said central portion of said bridging member, said fastening member is normally bowed in shape between its two ends as seen in a plane extending through said first and second sides and said two ends of said fastening member such that said first and second sides normally are convex and concave, respectfully, as seen in said plane extending through said first and second sides and said two ends of said fastening member, said hooks extend from said second side of said fastening member at its two ends in a direction generally transverse to the dimension of said fastening member between its two ends and then toward each other terminating in hook ends which generally face each other, the minimum distance between each set of said two apertures of said bridging member is greater than the distance between said two hook ends of said fastening member when said fastening member is in its normal bowed shape, the material of said fastening member being characterized such that force may be applied to said fastening member to straighten said fastening member and when the force is released, said fastening member resumes its normally bowed shape whereby said fastening member may be removably coupled to said bridging member by applying force to said fastening member to straighten said fastening member to increase the distance between said hook ends of said hooks to allow said hooks to be inserted into a selected one of said plurality of sets of said apertures of said bridging member and then releasing the force to allow said hooks to engage the structure of said bridging member which define the edges of said selected set of apertures closest to each other.

* * * * *